(12) United States Patent
Postelmans

(10) Patent No.: US 6,517,504 B1
(45) Date of Patent: Feb. 11, 2003

(54) KNEE-ASSISTING OR KNEE-SUBSTITUTE APPARATUS

(75) Inventor: Roberto Jean José Postelmans, Brussels (BE)

(73) Assignee: Magalie Postelmans, Brussels (BE)

( * ) Notice: Subject to any disclaimer, the term of this patent is extended or adjusted under 35 U.S.C. 154(b) by 0 days.

(21) Appl. No.: 09/890,207

(22) PCT Filed: Jan. 28, 2000

(86) PCT No.: PCT/BE00/00010

§ 371 (c)(1),
(2), (4) Date: Jul. 27, 2001

(87) PCT Pub. No.: WO00/44322

PCT Pub. Date: Aug. 3, 2000

(30) Foreign Application Priority Data

Jan. 29, 1999 (BE) ............................................. 09900057

(51) Int. Cl.$^7$ ................................................. A61F 5/00
(52) U.S. Cl. ........................................................ 602/26
(58) Field of Search ............................. 623/39; 602/16, 602/26

(56) References Cited

U.S. PATENT DOCUMENTS

| | | | |
|---|---|---|---|
| 2,883,982 A | | 4/1959 | Rainey |
| 3,779,654 A | * | 12/1973 | Horne |
| 5,009,223 A | * | 4/1991 | DeFonce ..................... 128/80 |
| 5,038,763 A | | 8/1991 | Wiggins |
| 5,107,824 A | * | 4/1992 | Rogers et al. |
| 5,230,696 A | * | 7/1993 | Silver et al. ................... 602/16 |
| 6,309,368 B1 | * | 10/2001 | Herzberg et al. ............. 602/26 |

FOREIGN PATENT DOCUMENTS

| | | | |
|---|---|---|---|
| DE | 196 05 734 | | 8/1997 |
| EP | 297 766 A1 | * | 1/1989 |
| EP | 0 884 035 | | 12/1998 |
| WO | WO 92/15264 | * | 9/1992 |
| WO | 9409729 | * | 5/1994 ................... 606/26 |

* cited by examiner

Primary Examiner—Eduardo C. Robert
(74) Attorney, Agent, or Firm—Sughrue Mion, PLLC

(57) ABSTRACT

A knee support or replacement appliance having, on at least one proximal section (5) of at least one joint, a first engagement surface which extends over the length of a trajectory corresponding to a displacement from an instantaneous center of movement formed by a projection of a crossover of the ligaments in the proximal section (5) during the movement of the knee. On at least one distal section (6) of the joint, there is a second engagement surface which extends over the length of a trajectory corresponding to the displacement from the instantaneous center of movement formed by a projection of the crossover of the ligaments in the distal section (6) during the relative movement of the knee. The second engagement surface is in apposition to the first engagement surface during this movement. Retention devices (23, 24) prevent mutual slippage between the first and second engagement surfaces during the movement of the knee.

12 Claims, 5 Drawing Sheets

KNEE-ASSISTING OR KNEE-SUBSTITUTE APPARATUS

BACKGROUND OF THE INVENTION

The present invention pertains to a knee support or replacement appliance, comprising at least one joint each consisting of at least one proximal section and at least one reciprocally articulated distal section, fixtures for attaching at least one proximal section of the said joint to a femoral part of a lower limb and at least one distal section of the said joint to a tibial part of the said lower limb, and guiding devices for the reciprocally articulated elements, allowing relative movement with flexion-extension, antero-posterior rolling in conjugation with slippage, rotation and/or varus between the said femoral and tibial parts, and thus allowing, looking laterally at the knee from an antero-posterior vertical plane, close-to-life reproduction of the physiological movement of the knee as achieved in the joint by the cruciate ligaments.

In terms of the invention, the term knee support appliance should be interpreted as a knee orthesis and the term replacement appliance as a knee prosthesis or endoprosthesis.

In the following document, the femoral and tibial parts of a lower limb refer not only to the parts of an existing limb but also the superior and/or inferior rigid sections replacing this limb.

The proximal section may therefore be adapted to a superior rigid section attached to the femur, or it may be extended for the length of the femur and be attached thereto, and the distal section may be adapted to an inferior rigid section attached to the tibia, or it may be extended for the length of the tibia and be attached thereto.

In the following document, flexion and extension refer to a relative movement between the femoral and tibial parts of a limb about a roughly horizontal axis traversing the knee schematically from left to right. Rotation refers to a relative movement between these parts about a vertical axis. Varus movement refers to a relative movement between these parts around an antero-posterior horizontal axis. Finally, rolling and antero-posterior slippage refer to a relative movement between the extremities of the tibial and femoral parts in an antero-posterior plane.

Ortheses are orthopaedic appliances which maintain movement and joint function of a deficient limb in a disabled person. Such appliances are made of two rigid parts, interlinked by a joint at the knee level, and fitted to one side or to both sides of the leg. The entire appliance may be attached with belts or moulds which run the length of the thigh and leg. Ortheses used for the lower limbs are customarily two symmetrical joints fitted at the knee, which allow them to move solely in flexion-extension with at best simultaneous antero-posterior displacement of the proximal part on the distal part (see EP-A-0297766, U.S. Pat. No. 3,779,654). Physiological movement of the knee is, however, three-dimensional, and these ortheses inevitably inevitably stress the ligaments, which defeats the purpose of any medical or surgical treatment.

We know from other sources that there are multiaxial ortheses fitted with grooved planar plates which operate in tandem, thus allowing the tibia to slide posteriorly in relation to the femur at the beginning of flexion followed by flexion without slippage (WO-A-92/15264).

There is also a polyaxial knee brace which is three-dimensional (see Orthotics Inc. Generation II polyaxial knee brace, Vancouver, Canada) and which comprises a joint which can be adjusted on one side of the deficient knee. In this joint, two spherical segments operate in tandem: they have two circularly arcuate grooves lying in an offset manner about an axis. In the initial degrees of flexion, the proximal section shifts, and once it reaches the limit of its grooved track, flexion continues over the groove on the second spherical segment, thus providing a three-dimensional if non-physiological movement. In fact, physiological movement of the knee, by means of the ligament rod system, comprises an antero-posterior rolling and slippage movement conjugated with rotation and varus movement. According to most medical studies, rotation and varus movement take place principally at the beginning of flexion, which this known appliance is not able to reproduce.

Another orthesis is known in which the guiding device is composed of grooved spherical shells which operate one inside the other (U.S. Pat. No. 5,107,824). In view of the fact that the center of the shells of the external joint of this appliance is situated at another position from the center of the shells of the internal joint the appliance is inevitably bound to block since the external and internal shells are also integrally interlinked by means of rigid belts around the thigh and leg. Moreover, the spherical shape of the shells and the fact that one is very snugly apposed to the other prevents a complex trajectory movement being obtained which mimics physiological movement of the knee.

Protheses are orthopaedic appliances which allow persons who have partially or totally lost their leg to remain ambulant. Fitted with a socket at the top and a joint at the level of the axis of the knee enabling flexion of the prosthesis, these appliances allow the disabled person to put weight on his stump. For femoral protheses for long amputation or amputation through the knee joint, it is impossible to position the prosthetic joint at its physiological site. The prosthetic joint is placed lower than the physiological axis of the knee, which makes walking uncomfortable and makes sitting look unaesthetic, since the thigh section is abnormally longer than the tibial section.

Finally, knee support or replacement appliances as described at the beginning of this document (see WO 94/09729) are known. These appliances, by means of a special configuration of the weight-bearing surfaces of the guiding devices of each joint, enable mutual movement of the articulated elements in the same way as is produced by a crossed rod system. Applied to curved, complex surfaces, it allows flexion to incorporate movements of rotation and varus simultaneously which vary in amplitude in proportion to the degree of flexion-extension.

During experiments with previously known appliances it emerged that, even in the best of the previously proposed solutions, joints were subject either to blocking of the guiding devices or to uncontrolled slippage between the articulated elements. This gives rise to excessively high wear of the guiding surfaces and to forcing of the ligaments in order to overcome the blocking of the mechanisms.

It is important to note that, in the present invention, a distinction is made between two types of "slippage" : "antero-posterior slippage" which has already been defined above and which involves a relative movement between tibia and femur, and "uncontrolled slippage of articulated elements" which relates solely to parts of the appliance.

SUMMARY OF THE INVENTION

The object of the present invention is to develop a knee support or replacement appliance such as would overcome the previously mentioned drawbacks and in particular aid the guiding of articulated elements in order to make it impossible for articulated elements to block or for reciprocal uncontrolled slippage to occur, while allowing physiological and relative movement between the femoral and tibial parts, in particular their antero-posterior slippage.

To solve these problems we have provided, according to the invention, a knee support or replacement appliance as described at the outset of the document, this appliance comprising in addition

- on at least one proximal section of at least one joint, a first engagement surface which extends over the length of a trajectory corresponding to a displacement from an instantaneous centre of movement formed by a projection of a crossover of the said ligaments in the said at least one proximal section during the said relative movement, and
- on at least one distal section of the said at least one joint, a second engagement surface which extends over the length of a trajectory corresponding to the displacement from the said instantaneous centre of movement formed by a projection of the said crossover of the said ligaments in the said at least one distal section during the said relative movement, and which is in apposition to the first engagement surface during this relative movement,
- and retention devices which prevent mutual slippage between the first and second engagement surfaces during the relative movement.

As has already been outlined, physiological movement of the knee involves several simultaneous movements, which is made possible by a special configuration of the bony extremities and by the fact that they are held together by the cruciate ligaments.

The appended FIG. 1 shows the antero-posterior plane of a knee G, seen from the side. In the position shown, the crossed rods AO and BC schematically represent the above-mentioned cruciate ligaments with the leg in the extended position. The letter a indicates the posterior cruciate ligament and the letter c the anterior cruciate ligament. The letter b (AB) represents the intercondylar roof, and the letter d (CO) the tibial plateau. The right part of the diagram is behind knee G, and is shown with a broken line.

The intercondylar roof AB is part of what is called in orthopaedic jargon the "fixed plane" and the tibial plateau OC is part of what is called the "mobile plane".

FIG. 1 shows three different displacement positions of the fixed plane relative to the mobile plane during relative movement of the knee, the mobile plane remaining stationary in this illustration.

As can be seen, the instantaneous centre of rotation of the fixed and mobile planes is the intersection I of the rods AO and BC. During displacement of the fixed plane as illustrated in FIG. 1 a curve is described by the successive positions of I in the mobile plane. This curve is termed the base and is marked IB.

This figure also shows the displacement positions of the mobile plane in relation to the fixed plane during relative movement of the knee, the fixed plane remaining stationary. Intersection I of the rods AO and BC thus takes up successive positions along a curve, termed the rolling curve, which is marked IR.

During mutual displacement of both planes, the rolling curve therefore rolls on the base without slippage over the kinematic plane: this results solely from the intersection of the crossed rods of the rod system which holds these planes together.

If these theoretical observations are applied to a knee joint, they signify that only the intersection of the cruciate ligaments produces a pure rolling movement. The further the centre of movement from this intersection the greater the amount of slippage in relation to rolling.

We have therefore planned according to the invention to apply to the joint(s) of the support or replacement appliance used proximal and distal sections, one moving on the other by means of engagement surfaces to the trajectories corresponding to the base and to the rolling curve of the movement of the cruciate ligaments. Moreover, to hinder any slippage between these surfaces, retention devices are provided. These devices and the trajectory of the engagement surfaces thus compel the instantaneous centre of the virtual rod system of their joint, which is a projection from the instantaneous centre of the cruciate ligaments in the sections of this joint, to follow a pure rolling trajectory: this avoids any inadvertent mutual slippage of the articulated elements and allows control of femoral and tibial slippage movements necessitated by the antero-posterior rolling of the relative movement of the knee.

According to one embodiment of the invention, the retention devices comprise the first enmeshing means mounted on the said first engagement surface on at least one part of this surface and the second enmeshing means mounted on the said second engagement surface on at least one part of this surface, and operating in tandem with the first enmeshing means during the said relative movement.

It should be noted that, in the case of enmeshing means operating in tandem, it may be considered, according to the invention, that the engagement surfaces of two proximal and distal sections are virtual and situated at the pitch lines of the enmeshing means.

According to an advantageous embodiment of the invention, the said first and second enmeshing means comprise cogs operating together in which a base of the teeth and an interdental space increase transversally to the said trajectory, moving from the inside to the outside of the joint.

As explained in detail in WO 94/09729, it is preferable that the two joints on either side of an antero-posterior plane should be different in order to enhance rotation and varus of the knee. As both these movements occur essentially at the beginning of flexion, it is therefore preferable that the teeth, in any event when the cogs start to engage, have a shape widening out towards the exterior.

According to a particular embodiment of the invention, the said first and second engagement surfaces are smooth. The retention devices may then advantageously comprise at least one belt presenting a first end and a second end, the first end of the said at least one belt being attached to one end of the said at least one proximal section close to an extremity of the said first engagement surface, the second end of the said at least one belt being attached to one end of the said at least one distal section close to an extremity of the said second engagement surface, situated facing the extremity of the first engagement surface to which the said at least one belt is attached to a proximal section.

Although it is not a prerequisite that the articulated elements of the appliances according to the invention allow rotation and varus, it is clearly preferable that they do so. Provision may therefore be made, as described for example in WO 94/09729, for the said guiding devices of each joint to comprise at least one guiding surface of predetermined curvature in an articulated element and at least one tracker element on the other articulated element and for these articulated elements to also have lateral appositional surfaces of predetermined curvature which operate together during the said relative movement between the femoral and tibial parts. It is to advantage that the said lateral appositional surfaces have mutually different complex curvatures by which they come only into partial contact, at least three points, during the movement between the femoral and tibial parts.

According to an improved embodiment of the invention, the trajectories of the said first and second enmeshing means extend in such a way as to fit the curvature of the respective articulated element on which they are fitted. The enmeshing means tend not to form rectilinear tracks over their entire length; in fact they follow complex curves corresponding to those set by the joint guiding devices, and do so in such a way as not to hinder the fairly physiological movement conferred by the guiding devices, while hindering any inadvertent slippage between the articulated elements.

Other embodiments of the invention are displayed in the claims appertaining to claim 1.

Other details and special features of the invention will appear in the description provided below in a non-limiting manner and with reference to the appended drawings.

DETAILED DESCRIPTION OF THE INVENTION.

Figure 1:
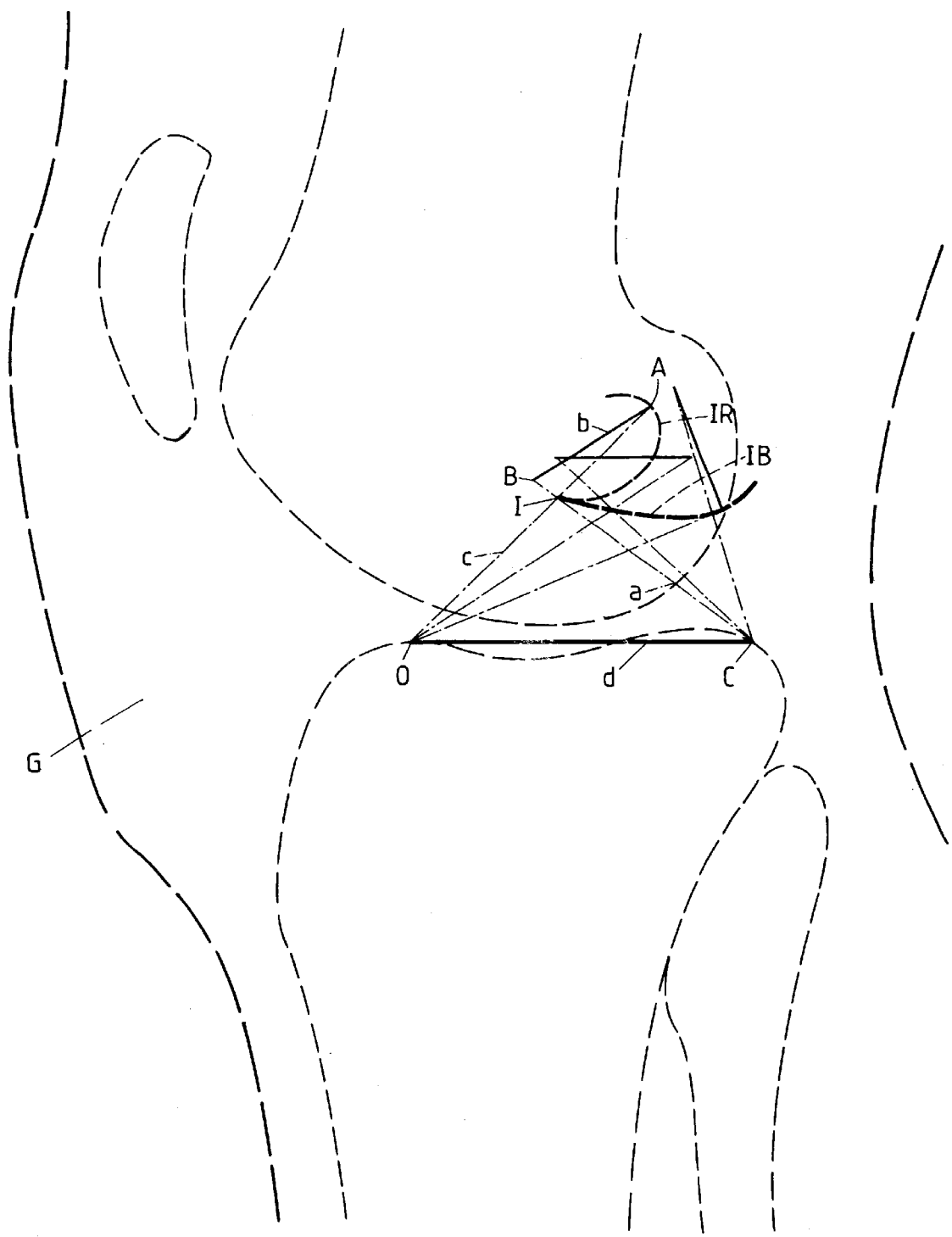
FIG. 1 shows a theoretical view of a projection in an antero-posterior vertical plane of the crossed rod system movement such as constituted by a knee joint.
Figure 2:
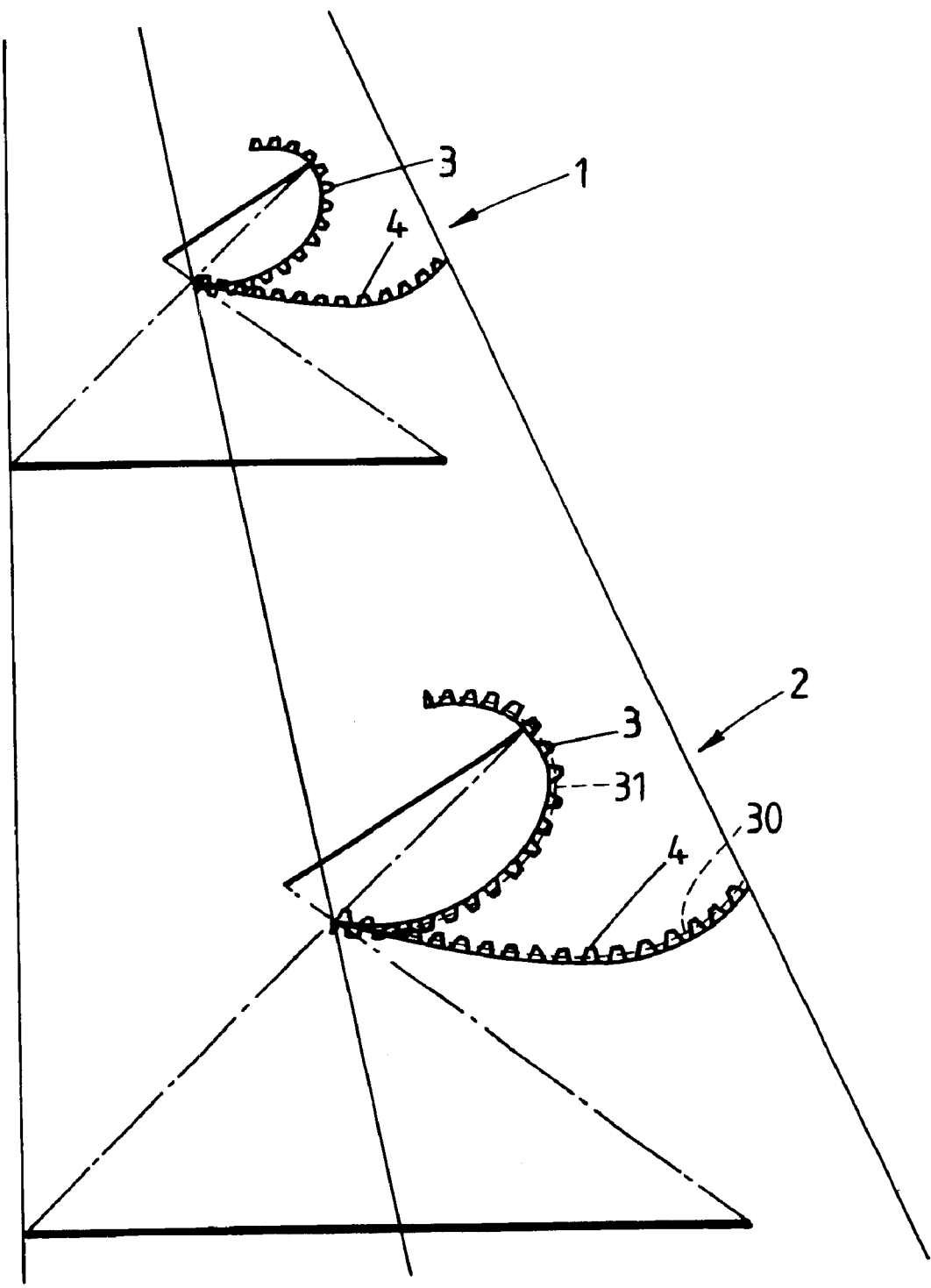
FIG. 2 shows in a perspective view a schematic double joint of an appliance according to the invention.

FIG. 2 illustrates a knee support or replacement appliance comprising a double joint 1 and 2 on either side of an antero-posterior vertical plane, extending by way of illustration but not obligatorily, through the centre of the knee. Provision can certainly be made for an appliance which comprises a single joint according to the invention.

As explained in detail in WO 94/09729, it is preferable that both joints 1 and 2 situated on either side of the knee are different in order to enhance rotation and varus. Accordingly, in the example given in FIG. 2, joint 1 situated on the inside of the knee is smaller than joint 2. Engagement surfaces 30 and 31 are arranged along the trajectories of the base and the rolling curve of each of the joints in such a way that the proximal and distal sections of each joint work together by mutual apposition at their instantaneous centre of movement.

Provision was made in this exemplary embodiment for retention devices to keep the engagement surfaces apposed to each other, without slippage, in the form of enmeshing means 3, 4 of the cog type. Consequently, the engagement surfaces in this example are virtual and correspond to the pitch lines 30, 31 of cogs 3 and 4. By means of these enmeshing means uncontrolled slippage between the articulated elements is no longer possible.

Figure 3:
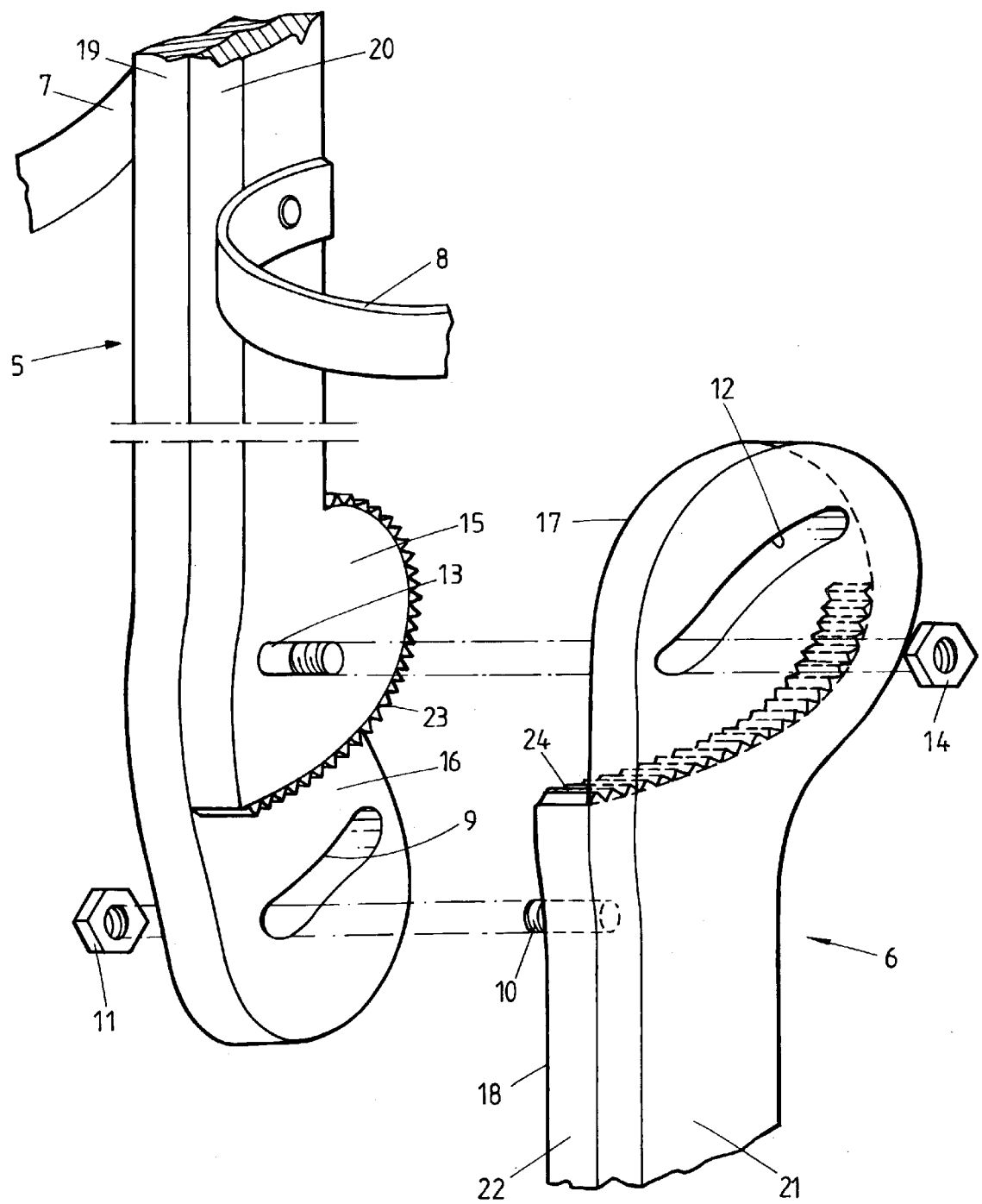
FIG. 3 shows a perspective view of an embodiment of the appliance according to the invention.

It should be understood that the engagement surfaces may be fitted with cogs over their entire length, as in the example illustrated in FIGS. 2 and 3, or solely over a part thereof.

FIG. 3 shows in exploded sections a joint comprising a proximal section 5 and a distal section 6 which are reciprocally articulated.

Fixtures 7 are shown in part; they enable the proximal section 5 to be attached to a femoral part of a lower limb. Similar or different fixtures, not shown, are provided for attaching the distal section 6 to a tibial part of this lower limb. The type of these fixtures is not critical and may be a belt, a strap or similar elements.

If the appliance comprises several joints, provision can be made for fixtures 8 to bind the proximal sections of the joints to each other; similarly provision can be made for fixtures (not shown) to bind the distal sections of the joints to each other. These fixtures may be rigid or supple structures. They are in any case not absolutely essential.

Provision is always made for guiding devices in the joints of prostheses and ortheses. As explained above, some guiding devices allow flexion only, and antero-posterior rolling combined with slippage. Other guiding devices further allow rotation and varus, which gives rise to a type of movement which is closer still to physiological movement.

The joint illustrated in FIG. 3 has guiding devices of the type provided for in WO 94/09729.

Proximal section 5 illustrated in FIG. 3 comprises, as guiding devices, a guiding surface formed by a groove 9 of complex curvature in which can be slotted a tracker element 10 in the form of a dowel pin extending from distal section 6. This tracker 10 is held in the groove 9 by a bolt 11 in such a way as to allow it to slide in the groove 9.

Distal section 6 illustrated in FIG. 3 comprises, as guiding devices, a guiding surface formed by a groove 12 of complex curvature in which can be slotted a tracker element 13 in the form of a dowel pin extending from proximal section 5. This tracker 13 is held in the groove 12 by a bolt 14 in such a way as to allow it to slide in the groove 12.

Proximal section 5 and distal section 6 also present lateral appositional surfaces 15, 16 which stand mutually opposed to those on the other side, respectively 17, 18. The surfaces of the illustrated example are not planar, and they have mutually different complex curvatures by which they come only into partial contact, at least three points, during the movement between the femoral and tibial parts of the limb, as is described in detail particularly in WO 94/09729.

In the exemplary embodiment illustrated, proximal section 5 consists of two plates 19, 20 fused to each other in some way, e.g. by bonding or welding. Plate 20 terminates at its lower border in a cog 23 the pitch line of which extends along the curvature of the rolling curve 31 which follows the instantaneous centre of the movement in this plate, plate 19 projecting slightly below the level of plate 15 where groove 9 and the lateral appositional surface 16 are to be found.

Similarly distal section 6 consists of two plates 21 and 22 also fused to each other in some way. Plate 22 terminates at its upper border in a cog 24 the pitch line of which extends along the curvature of the base 30 which follows the instantaneous centre of the movement in this plate, plate 21 projecting slightly above the level of plate 22 where groove 12 and the lateral appositional surface 17 are to be found.

Along these lower and upper borders of plates 20 and 22 respectively, cogs 23 and 24 are able to operate together when the sections are assembled and their engagement surfaces at the level of the pitch lines 30 and 31 of the cogs 23 and 24 subjected to relative movement. The respective lateral appositional surfaces 16 and 18, and 15 and 17, can then operate together too.

The known guiding devices will therefore transmit, at the joint and at the knee to which the appliance is attached, a rod-type movement enabling rotation and varus. According to the invention, the instantaneous centre of movement of the rod will be compelled, by the cogs, to follow a pure rolling movement. Accordingly, uncontrolled slipping movements and inadvertent blockages of the dowel pins in the grooves which occured at certain junctures in appliances built according to the prior art will disappear.

It may be noted that the gear teeth fitted to the circular surfaces in one joint of the knee support appliance are known (see U.S. Pat. No. 2,883,982, U.S. Pat. No. 3,779, 654, U.S. Pat. No. 5,038,763 and DE-A-19605734). However, these cogs are not ordered along the trajectory of the instantaneous centre of the joint and they therefore force the knee. Moreover, the way in which they are produced generally does not permit anything other than a flexion-extension movement and non-physiological antero-posterior rolling.

Figure 4:
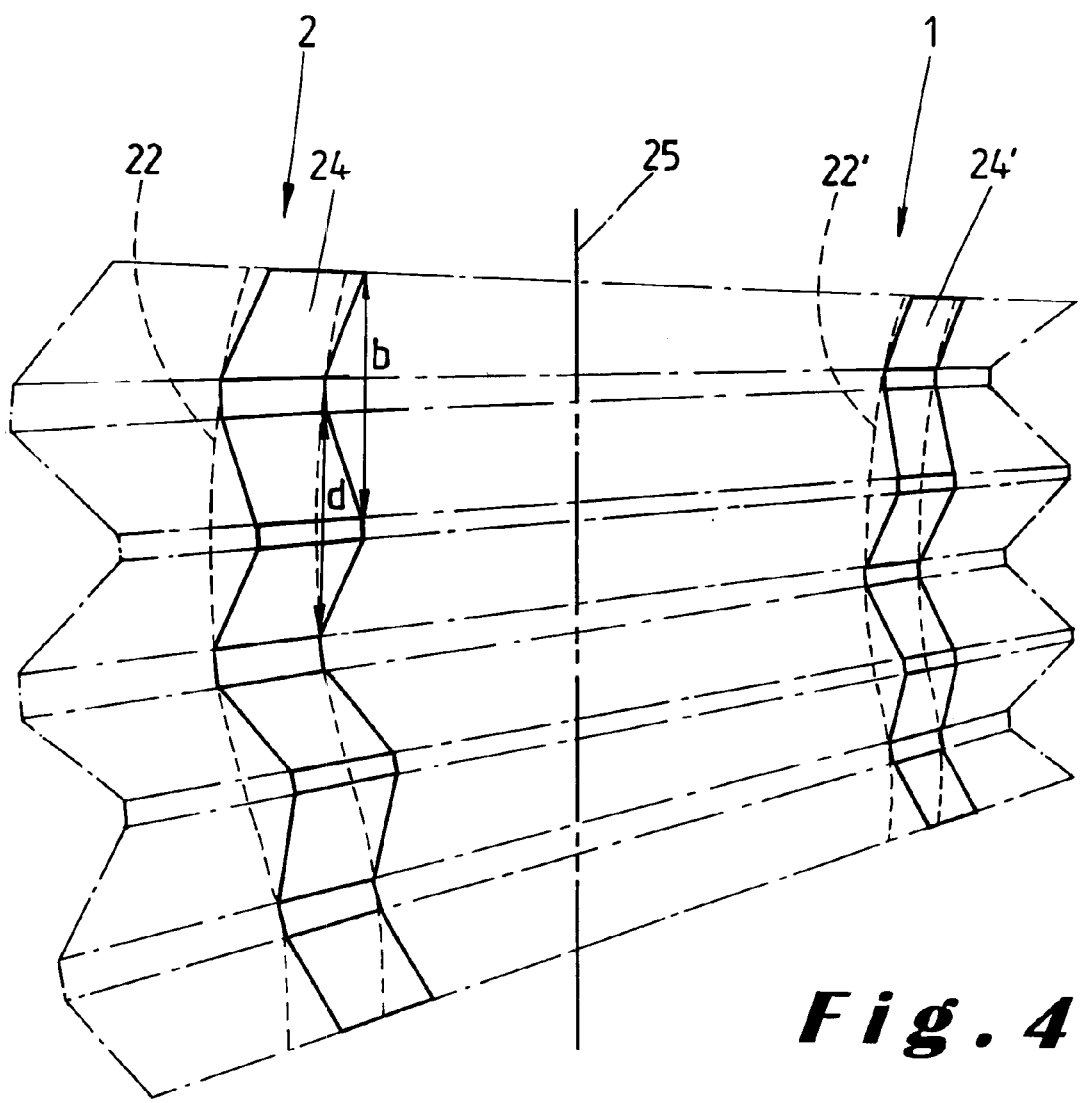
FIG. 4 shows a perspective view of two enmeshing means according to the invention.

FIG. 4 shows a perspective view from above of a part of the cogs 24, 24' fitted along the base of each of the two joints 1 and 2 situated on either side of an antero-posterior plane 25.

These cogs 24, 24' are ordered along the upper border of a plate 22 and 22' respectively of each of the distal sections of the corresponding joint. The upper border of these plates is illustrated in FIG. 4 by a broken line which follows a circuitous track corresponding to the complex curved shape of the distal sections.

On the right-hand side of FIG. 4, joint 1 is situated more internally, i.e. closest to the antero-posterior plane dividing the structure in two. As can be seen the cogs 24' differ from the cogs 24. The interdental space b, i.e. the space from the top of a tooth on the cogs to the top of the next tooth increases the further away from the plane dividing the structure in two, i.e. the more externally the cogs are situated. Similarly, on the same cogs, the interdental space widens out transversally towards the exterior. In the same way, the base of the teeth d, i.e. the distance between the bottom of the side of a tooth and the bottom of the opposite side of this tooth increases the more externally the cogs are situated. It also increases transversally towards the exterior in the same cogs.

The corresponding cogs are arranged along the lower border of the proximal sections.

The complex curved shape of the cogs and the increase in the interdental space and in the size of the base of the teeth proportionally to the increasing distance between the cogs and the plane dividing the structure in two enable the cogs to roll perfectly, while controlling any relative movement of the joints in a perfectly physiological way.

It should be understood that the present invention is not limited to the embodiments described above and that considerable modifications may be introduced to it without departing from the context established by the appended claims.

It is apparent that plates 19 and 20 and plates 21 and 22 respectively are not absolutely required to form together an integral structure 5 or 6. It is feasible that plates 19 and 21 could serve solely for joint guidance and a separate mechanism formed by plates 20 and 22 could serve solely for rolling of the instantaneous centre and therefore for controlling the guiding devices.

Although the joint illustrated in FIG. 3 is an orthetic joint, a person skilled in the art will immediately realize its application for a prosthetic device.

It is of advantage that over the terminal part of the cogs, i.e. the part which corresponds to the completion of flexion, the interdental space b and the base of the teeth d may become constant, since it is known that, in this segment of relative movement of the knee, there is no longer any variation in rotation or varus movement.

It is also possible to envisage guiding surfaces in the shape of a single groove in only one of the joint sections, e.g. a groove 9 or 12, with a single corresponding tracker element 10 or 13, respectively. The presence of enmeshing means is enough to ensure that corresponding guiding surfaces on the other joint section are not absolutely necessary.

It is also feasible for the plates fitted with cogs to be planar and not present any complex curvatures. In this case the cogs could have an interdental space and a tooth root of constant dimensions.

Figure 5:
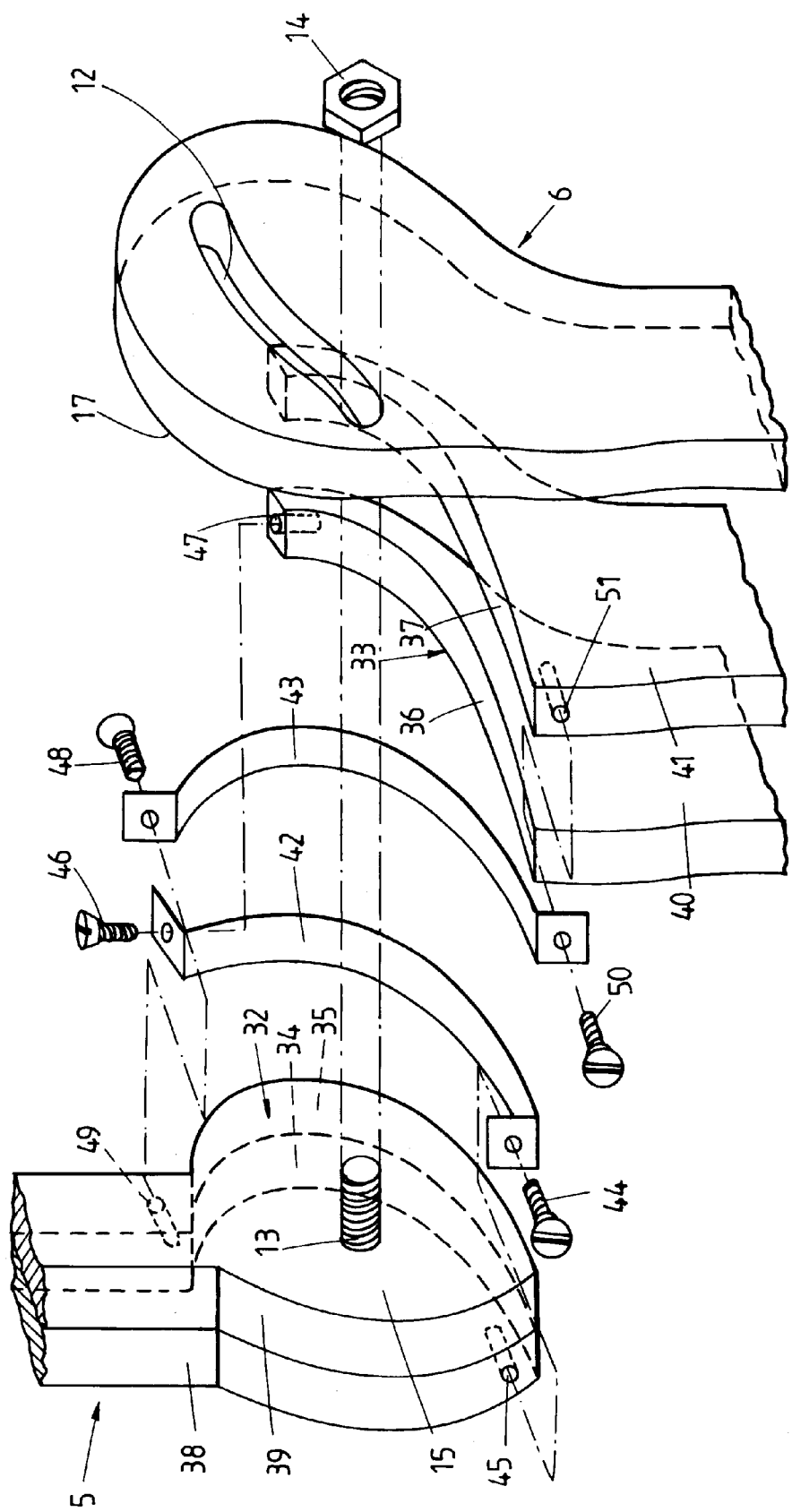
FIG. 5 shows an exploded perspective view of a variant version of the appliance according to the invention.

FIG. 5 shows an appliance, according to the invention, in which the engagement surfaces 32 and 33 are smooth. Each of these surfaces consists of two tracks 34, 35 and 36, 37, respectively, which are situated at the end of plates 38, 39 and 40, 41, respectively, and which extend along the trajectory of the instantaneous centre in their respective section during flexion of the knee.

The retention devices which hinder slippage between the engagement surfaces of the proximal section 5 and the distal section 6 consist in the illustrated example of two belts 42 and 43.

The belt 42 is attached at one end to plate 38 of the proximal section 5 by means of a screw bolt 44 screwed into a tapped hole 45 in the plate close to one edge of the meshing track 34. At the other end it is attached to plate 40 of the distal section 6 by means of a screw bolt 46 screwed into a tapped hole 47 in the plate close to one edge of the meshing track 36 which is situated facing the edge of the meshing track 34 to which the belt 42 is attached.

The belt 43 is attached at one end to plate 39 of the proximal section 5 by means of a screw bolt 48 screwed into a tapped hole 49 in the plate close to one edge of the meshing track 35. At the other end it is attached to plate 41 of the distal section 6 by means of a screw bolt 50 screwed into a tapped hole 51 in the plate close to one edge of the meshing track 37 which is situated facing the edge of the meshing track 35 to which the belt 43 is attached. Although plates 40 and 41 have been shown in exploded form, it should be noted that, in the illustrated example, they are fused to each other as are plates 38 and 39. The arrangement of the belts between the plates enables any slippage between the sections to be avoided during movement of the joint, while the instantaneous centre of the rod-system performs a pure rolling movement. During this movement, belts 42 and 43 are enclosed between the first and second engagement surfaces 32 and 33.

In the illustrated example, only the distal section has a guiding surface in the shape of a groove 12, in which the tracker 13 of the proximal section 5 may slide. The lateral appositional surfaces 15 and 17 which stand mutually across from each other are, in this example, perfectly planar.

What is claimed is:

1. A knee support or replacement appliance, comprising:
   at least one joint (1, 2) having at least one proximal section (5) and at least one reciprocally articulated distal section (6),
   fixtures (7) for attaching said at least one proximal section (5) of said joint to a femoral part of a lower limb and said at least one distal section (6) of said joint to a tibial part of the lower limb,
   guiding devices for said reciprocally articulated proximal and distal sections, allowing relative movement with flexion-extension, antero-posterior rolling in conjugation with slippage, rotation varus between the femoral and tibial parts, and thus allowing, looking laterally at the knee from an antero-posterior vertical plane, close-to-life reproduction of physiological movement of the knee as achieved in the joint by cruciate ligaments, on said at least one proximal section (5) of said at least one joint (1, 2), a first engagement surface (31, 32) which extends over a length of a trajectory corresponding to a displacement from an instantaneous centre of movement formed by a projection of a crossover of the ligaments in said at least one proximal section (5) during said relative movement, on said at least one distal section (6) of said at least one joint (1, 2), a second engagement surface (30, 33) which extends over the length of a trajectory corresponding to the displacement from said instantaneous centre of movement formed by a projection of said crossover of the ligaments in said at least one distal section (6) during said relative movement, and which is in apposition to the first engagement surface during this relative movement, retention devices which prevent mutual slippage between the first and second engagement surfaces (30, 31, 32, 33) during the relative movement.

2. Appliance according to claim 1, characterized in that the retention devices comprise first enmeshing means (3, 23) mounted on the said first engagement surface (31) on at least one part of this surface and second enmeshing means (4, 24, 24') mounted on the said second engagement surface (30) on at least one part of this surface, and operating in tandem with the first enmeshing means during the said relative movement.

3. Appliance according to claim 2, characterized in that the said first and second enmeshing means (3, 23; 4, 24, 24') comprise cogs operating together in which a tooth root (d) and an interdental space (b) increase transversally to the said trajectory, moving from the inside to the outside of the joint.

4. Appliance according to claim 2, characterized in that said guiding devices and said first enmeshing means (3, 23) are on said proximal section (5) of said joint.

5. Appliance according to claim 2, characterized in that said guiding devices and said second enmeshing means (4, 24, 24') are on said distal section (6) of a joint.

6. Appliance according to claim 1, characterized in that the said first and second engagement surfaces (32, 33) are smooth.

7. Appliance according to claim 6, characterized in that the retention devices comprise at least one belt (42, 43) presenting a first end and a second end, and in that the first end of the said at least one belt (42, 43) is attached to one of the said at least one proximal section (5) close to an extremity of the said first engagement surface (32), the second end of the said at least one belt (42, 43) being attached to one of the said at least one distal section (6) close to an extremity of the said second engagement surface (33), situated facing the extremity of the first engagement surface to which the said at least one belt (42, 43) is attached to a proximal section.

8. Appliance according to claim 7, characterized in that each abovementioned belt (42, 43) is enclosed between the first and second engagement surfaces (32, 33) during the abovementioned relative movement.

9. Appliance according to claim 1, characterized in that the said guiding devices of each joint comprise at least one guiding surface (9, 12) of predetermined curvature in an articulated element and at least one tracker element (10, 13) on the other articulated element, and in that these articulated elements also have lateral appositional surfaces (15, 16, 17, 18) of predetermined curvature which operate together during the said relative movement between the femoral and tibial parts.

10. Appliance according to claim 9, characterized in that the said lateral appositional surfaces (15, 16, 17, 18) have mutually different complex curvatures by which they come only into partial contact, at least three points, during the movement between the femoral and tibial parts.

11. Knee support or replacement appliance according to claim 1, comprising at least one abovementioned joint and at least one other abovementioned joint situated on either side of an antero-posterior vertical plane.

12. Appliance according to claim 11, comprising a first fixation device (8) for reciprocal attachment of said proximal section of the joint, and a second fixation device for reciprocal attachment of said distal section of the joint.

* * * * *